(12) United States Patent
Adey et al.

(10) Patent No.: US 8,501,115 B2
(45) Date of Patent: Aug. 6, 2013

(54) MODULAR SYSTEM FOR PERFORMING LABORATORY PROTOCOLS AND ASSOCIATED METHODS

(75) Inventors: Nils Adey, Salt Lake City, UT (US); Rob Parry, Park City, UT (US)

(73) Assignee: Statspin, Inc., Westwood, MA (US)

( * ) Notice: Subject to any disclaimer, the term of this patent is extended or adjusted under 35 U.S.C. 154(b) by 363 days.

(21) Appl. No.: 12/606,083

(22) Filed: Oct. 26, 2009

(65) Prior Publication Data
US 2010/0113288 A1    May 6, 2010

Related U.S. Application Data

(60) Provisional application No. 61/108,402, filed on Oct. 24, 2008, provisional application No. 61/171,042, filed on Apr. 20, 2009, provisional application No. 61/228,040, filed on Jul. 23, 2009.

(51) Int. Cl.
*B01L 99/00* (2010.01)

(52) U.S. Cl.
USPC ........... 422/500; 422/501; 422/509; 422/565; 422/63; 422/68.1; 422/81

(58) Field of Classification Search
USPC .................. 422/500, 501, 509, 565, 63, 68.1, 422/81
See application file for complete search history.

(56) References Cited

U.S. PATENT DOCUMENTS

| | | | |
|---|---|---|---|
| 5,061,630 A | 10/1991 | Knopf et al. | |
| 5,104,621 A | 4/1992 | Pfost et al. | |
| 5,167,615 A | 12/1992 | East et al. | |
| 5,231,029 A | 7/1993 | Wootton et al. | |
| 5,437,838 A | 8/1995 | DeMoranville et al. | |
| 5,443,791 A | 8/1995 | Cathcart et al. | |
| 5,625,706 A | 4/1997 | Lee et al. | |
| 5,637,208 A | 6/1997 | Dourdeville | |
| 5,695,720 A | 12/1997 | Wade et al. | |
| 5,897,781 A | 4/1999 | Dourdeville | |
| 5,993,654 A | 11/1999 | Black | |
| 6,180,061 B1 | 1/2001 | Bogen et al. | |

(Continued)

FOREIGN PATENT DOCUMENTS

| | | |
|---|---|---|
| WO | WO 95-05590 | 2/1995 |
| WO | WO 2010/048631 | 4/2010 |

OTHER PUBLICATIONS

Steven Q. Irvine "Whole-mount in situ hybridization of small invertebrate embryos using laboratory mini-columns" BioTechniques. vol. 43, No. 6, 2007. pp. 764-768.

*Primary Examiner* — Jill Warden
*Assistant Examiner* — Monique Cole
(74) *Attorney, Agent, or Firm* — Preti Flaherty Beliveau & Pachios LLP

(57) ABSTRACT

Systems, devices, and methods for automating laboratory protocols utilizing modular processing components to allow systems to be reconfigured for processing a wide variety of disparate laboratory protocols are provided. In one aspect, a sample processing module is provided, including a housing configured to accommodate a pre-identified sample process, a standardized temperature input capable of interfacing with a temperature controller, a standardized fluid input capable of interfacing with an input fluid controller, and a standardized agitation connector capable of interfacing with an agitator. These standardized components provide interchangeability of the module with a module having a housing configured to accommodate a different pre-identified sample process in a sample processing system.

24 Claims, 11 Drawing Sheets

U.S. PATENT DOCUMENTS

| | | |
|---|---|---|
| 6,212,705 B1 | 4/2001 | Kramer |
| 6,235,479 B1 | 5/2001 | Rogers |
| 6,238,910 B1 | 5/2001 | Custance et al. |
| 6,296,809 B1 | 10/2001 | Richards et al. |
| 6,432,696 B2 | 8/2002 | Custance et al. |
| 6,485,913 B1 | 11/2002 | Becker et al. |
| 6,607,907 B2 | 8/2003 | McNeely et al. |
| 6,615,856 B2 | 9/2003 | McNeely et al. |
| 6,637,463 B1 | 10/2003 | Lei et al. |
| 6,663,353 B2 | 12/2003 | Lipscomb et al. |
| 6,793,890 B2 | 9/2004 | Morales et al. |
| 6,810,805 B1 | 11/2004 | Atwater |
| 6,827,901 B2 | 12/2004 | Copeland et al. |
| 6,881,579 B2 | 4/2005 | Hilson et al. |
| 7,013,978 B2 | 3/2006 | Appleford et al. |
| 7,056,477 B1 | 6/2006 | Schwalbe et al. |
| 7,223,363 B2 | 5/2007 | McNeely et al. |
| 7,235,400 B2 | 6/2007 | Adey |
| 7,358,078 B2 | 4/2008 | Chen et al. |
| 7,390,458 B2 | 6/2008 | Burow et al. |
| 7,468,161 B2 | 12/2008 | Reinhardt et al. |
| 7,557,070 B2 | 7/2009 | Ravkin et al. |
| 7,612,020 B2 | 11/2009 | Stuelpnagel et al. |
| 7,614,857 B2 | 11/2009 | Fuechslin et al. |
| 7,964,413 B2 * | 6/2011 | Macioszek et al. ............ 436/165 |
| 7,985,375 B2 * | 7/2011 | Edens et al. .................... 422/64 |
| 2005/0239195 A1 | 10/2005 | Oram et al. |
| 2006/0088451 A1 | 4/2006 | Nakajima et al. |
| 2006/0141635 A1 | 6/2006 | Taneike |
| 2008/0014576 A1 | 1/2008 | Jovanovich et al. |
| 2008/0247914 A1 * | 10/2008 | Edens et al. .................. 422/100 |
| 2010/0167943 A1 | 7/2010 | Adey et al. |
| 2010/0200021 A1 | 8/2010 | Adey et al. |

* cited by examiner

MODULAR SYSTEM FOR PERFORMING LABORATORY PROTOCOLS AND ASSOCIATED METHODS

PRIORITY DATA

This application claims the benefit of U.S. Provisional Patent Application Ser. Nos. 61/108,402, 61/171,042, and 61/228,040, filed on Oct. 24, 2008, Apr. 20, 2009, and Jul. 23, 2009 respectively, each of which are incorporated herein by reference.

FIELD OF THE INVENTION

The present invention relates generally to systems, devices, and methods for performing laboratory protocols and associated methods. Accordingly, the present application involves the fields of biology, physics, and chemistry.

BACKGROUND

A large number of analytical methods and tools exist today in the scientific work place that can be used for testing samples of a wide variety. Examples of such tools include various forms of chromatography, Polymerase Chain Reaction (PCR), micro array hybridizations, flow cytometry, etc., utilize a number of different equipment types. While the equipment in support of such testing has come into being and greatly evolved over recent years, many short comings and challenges still exist. For example, such instrumentation is most often multi-piece and requires a significant amount of space. In addition, the various components must all be separately monitored and maintained and can cause unpleasant issues regarding running, and maintaining the instrument. Further, most instrumentation is able to perform only one basic operation and type of analysis. Finally, many analytical devices must be manually operated throughout a significant portion of the analytical procedures being performed.

SUMMARY

The present invention provides systems, devices, and methods for automating laboratory protocols. Furthermore, these systems and methods utilize modular processing components to allow systems to be reconfigured for processing a wide variety of disparate laboratory protocols and analytical methods. In one aspect, for example, a sample processing module is provided. Such a module can include a housing configured to accommodate a pre-identified sample process, a standardized temperature input capable of interfacing with a temperature controller, a standardized fluid input capable of interfacing with an input fluid controller, and a standardized agitation connector capable of interfacing with an agitator. These standardized components provide interchangeability of the module with a module having a housing configured to accommodate a different pre-identified sample process in a sample processing system.

In addition to the variability provided by the interchangeability of modules, the modules themselves can contain variable components. For example, in one aspect, the housing of the module includes an internal space to accommodate the pre-identified sample process. In a more specific aspect, the module can further include a sample process insert configured to insert into the internal space. Thus for a given module, the sample process insert can be interchangeable to allow further variability. Non-limiting examples of sample process inserts can include a microscope slide, a microarray, a sample basket, a blot, a filter, an ELISA insert, and the like, including combinations thereof.

Furthermore, the module can accommodate a variety of sample processes, and any sample process that is capable of being automated is considered to be within the present scope. Non-limiting examples of sample processes include in situ hybridizations such as fluorescent in situ hybridization (FISH) and whole mount in situ hybridization (WISH), blots such as Western blots, Northern blots, and Southern blots, slide processing, immunohisto chemistry reactions, histopathology reactions, antibody assays, electrophoresis, restriction analysis, ligation, labeling, labeling reactions for large or medium scale probe synthesis, DNA/RNA/microRNA labeling reactions, filter-based assays, and the like, including combinations thereof.

The present invention additionally provides systems for performing a laboratory protocol. In one aspect, such a system can include at least one sample processing module as described herein. The system can include a temperature control system interfaced with the standardized temperature input and configured to regulate temperature of the pre-identified sample process, an inlet fluid controller interfaced with the standardized fluid input and configured to deliver fluid to the pre-identified sample process, and an agitator interface with the sample processing module and configured to provide agitation to the pre-identified sample process. Additionally, a control system can be interfaced with the temperature control system, the inlet fluid controller, and the agitator, and configured to control temperature, fluidics, and agitation of the pre-identified sample process. In another aspect, the at least one sample processing module is a plurality of sample processing modules. In yet another aspect, at least two of the plurality of sample processing modules have a different pre-identified sample process.

DETAILED DESCRIPTION

Figure 1:
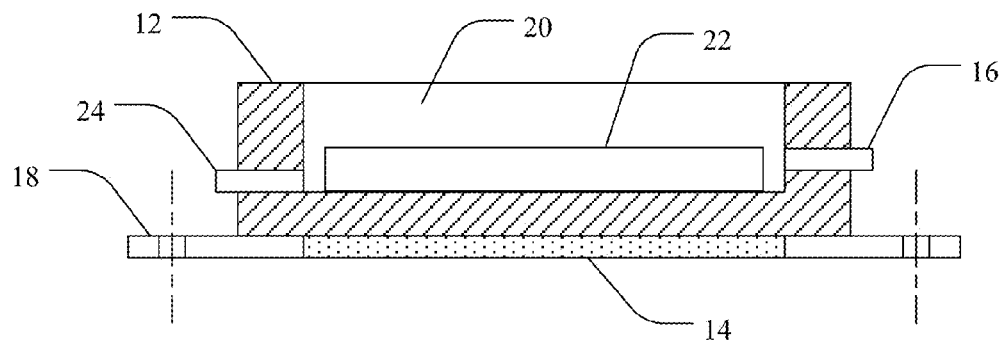
FIG. 1 is a cross-sectional view of sample processing module in accordance with one embodiment of the present invention.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a buffer" includes one or more of such buffers, and reference to "the chemical" includes reference to one or more of such chemicals.

Definitions

In describing and claiming the present invention, the following terminology will be used in accordance with the definitions set forth below.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The Invention

The present invention provides systems, devices, and methods for automating laboratory protocols that utilize modular processing components to allow systems to be reconfigured for processing a wide variety of disparate laboratory protocols. A modular system integrating various modules for performing various portions of a laboratory protocol can often increase the efficiency, accuracy, and consistency of lab work. A variety of modules and components are contemplated, and it should be understood that a given collection of modules and components can vary depending on the protocol being performed and any preferences of the individual performing the procedures. One advantage of such a system is the ease and convenience of operation and reconfiguration. Modules can be easily swapped out and replaced as they wear out, or as protocol conditions change. Equipment upgrades can be accomplished by merely switching old modules for updated modules, thus reducing the need to purchase an entirely new system. Additionally, system setups for different protocols can merely entail switching modules and reagents.

In one aspect of the present invention, a sample processing module is provided. As is shown in FIG. 1, for example, a sample processing module can include a housing 12 configured to accommodate a pre-identified sample process, a standardized temperature input 14 capable of interfacing with a temperature controller, a standardized fluid input 16 capable of interfacing with an input fluid controller, and a standardized agitation connector 18 capable of interfacing with an agitator. The standardized components provide interchangeability of the module with a module having a housing configured to accommodate a different pre-identified sample process in a sample processing system. In other words, the various connections and fittings are designed to allow a module having a given sample process to be replaced by a module having a different sample process, while allowing the standardized components to interface with the proper components of the system.

In another aspect, the housing includes an internal space 20 to accommodate the pre-identified sample process. Such an internal space allows the introduction and retention of fluids around a sample for the performance of a laboratory protocol. Thus fluid reagents, fluid washes, buffers, and the like can be contained within the internal space during heating, cooling, agitation, or any other protocol step. Furthermore, the internal space can receive and contain a sample process insert 22 during the laboratory protocol. Sample process inserts can provide further variability to the system, allowing further flexibility in the types of laboratory protocols to be performed using one type of sample module. The present scope should include any type of sample insert configured to be received into the internal space. Non-limiting examples of such inserts can include microscope slides, microarrays, sample baskets, blots, filter, ELISA inserts, and the like, including and combinations thereof.

It is contemplated that numerous sample processes can be performed using the modules according to aspects of the present invention, and any sample process that can be performed in a module is considered to be within the present scope. A sample process can be a laboratory protocol, or a portion of a laboratory protocol. In other words, in one aspect, a sample process can encompass all of or substantially all of a laboratory protocol. As such, a sample can be introduced into a module, and a laboratory protocol can be performed thereon from start to finished product. In another aspect, a sample process can encompass a portion of a laboratory protocol. For example, a sample process can be merely a series of wash and reaction steps that are only a part of a laboratory protocol, the rest of which is performed outside of a sample module. In another aspect, a sample process that is a first portion of a laboratory protocol can be performed in one sample module, and a different sample process that is a second portion of the laboratory protocol can be performed in a different sample module. Non-limiting examples of sample processes can include in situ hybridizations such as fluorescent in situ hybridization (FISH) and whole mount in situ hybridization (WISH), blots such as Western blots, Northern blots, Southern blots, slide processing, immunohisto chemistry reactions, histopathology reactions, antibody assays, gel electrophoresis, restriction analysis, ligation, labeling, filter-based assays, and the like, including combinations thereof. In one specific aspect, the sample process can be a FISH process. In another specific aspect, the sample process can be a WISH process.

Returning to FIG. 1, the standardized fluid input 16 is configured to allow fluid to enter the internal space 20 of the sample processing module from the input fluid controller. In one aspect, the standardized fluid input can be a coupling, fitting, channel, or other fluidic structure that penetrates the housing 12 of the sample module. In such cases, the input fluid controller can be coupled to the coupling, fitting, channel or other fluidic structure directly or via fluidic tubing in order to provide fluid to the internal space. In one specific aspect, the standardized fluid input is configured to fluidically couple with a fluid line, and the input fluid controller is a pump system. In another aspect, the standardized fluid input can be an open receptacle of the sample module, and the input controller can be a pipette (not shown). In those aspects wherein the housing has an internal space, the open receptacle can be an open portion of the housing providing access to the internal space.

The sample processing module can also include a standardized fluid output 24 capable of interfacing with an output fluid controller. In one aspect, the standardized fluid output can be a coupling, fitting, channel, or other fluidic structure that penetrates the housing 16 of the sample processing module. In such cases, the output fluid controller can be coupled to the coupling, fitting, channel or other fluidic structure directly or via fluidic tubing in order to remove fluid from the internal space. In one specific aspect, the standardized fluid output is configured to fluidically couple with a fluid line, and the output fluid controller is a pump system, or any other system that provides a vacuum force to the fluid line. In some cases, gravity or capillary forces can be used in lieu of a pump to draw fluid from the internal space. In another aspect, the standardized fluid output can be an open receptacle of the sample module, and the output controller can be a pipette (not shown). In those aspects wherein the housing has an internal space, the open receptacle can be an open portion of the housing providing access to the internal space.

Various configurations for the standardized temperature input 14 are contemplated, and any temperature input capable of regulating the temperature of the sample process should be considered to be within the present scope. The temperature input is a thermally conductive area of the sample processing module that is capable of interfacing with a temperature controller in order to regulate the temperature of the sample process. In those aspects having an internal space, the standardized temperature input is configured to provide temperature regulation to the internal space. In one aspect, the standardized temperature input can be a thermally conductive material associated with the housing in a position that allows thermal regulation to occur. The material of the standardized temperature input can be any thermally conductive material, such as, for example, materials that can be used in common heat spreaders. Various metals can be used, such as aluminum, copper, or any other thermally conductive metal, including associated alloys. Additionally, thermally conductive non-metals can also be utilized. Non-limiting examples include diamond-like carbon, graphite materials, and the like.

In one aspect, the heating and/or cooling element can reside in the standardized temperature input 14, and the temperature controller can merely control the heating and/or cooling element. One non-limiting example of such elements includes one or more Peltier elements thermally coupled to a heat spreading surface. Thus the temperature controller provides electrical input to the Peltier elements in order to regulate heating or cooling of the sample processing module. In the case of a Peltier device, current delivered thereto causes one side of the device to heat and the other side to cool. Reversing the polarity of the current causes a reversal in which side is heated and which side is cooled. Thus by coupling such devices to the standardized temperature input, the sample processing module temperature can be controlled. Such control can include maintaining a given temperature during a reaction, providing heating or cooling to the reaction, cycling the temperature during the reaction, and the like. Fans can be associated with the Peltier elements to dissipate heat or cold from the side of the Peltier device that is not controlling the temperature of the reaction. For example, if the sample processing module is being cooled, the downward side becomes hot, and thus the fans function to cool the non-functional side of the Peltier. Thermal fins can also be associated with the Peltier materials to assist in this thermal regulation. It should also be noted that the thermal cooling devices can function dependently to control temperature uniformly across all of the sample modules, or they can function independently to control temperature differently for different sample modules. In another aspect, the heating and/or cooling element can reside in the temperature controller. In this case, heating and/or cooling are generated at the temperature controller and thermally transferred to the standardize temperature input. Such heating and cooling can occur by any known technique, such as Peltier elements, conductive heat elements, convective heat elements, fluidic heat elements, and the like.

The housing 12 of the sample processing module can be made from a variety of materials. The interface between the sample process and the housing should be substantially inert with respect to the sample process. As such, the housing material itself can be substantially inert, or a coating can be applied to any surfaces of the housing or internal space that will come in contact with the materials of the sample process. Generally, however, the housing can be made from metals, such as aluminum, copper, stainless steel, nickel, and alloys thereof, from polymeric materials, ceramics, and the like. Coatings for protective purposed can include modified surfaces such as anodized layers on an aluminum surface, or polymeric or other inert coatings that can provide adequate protection between the housing material and the sample process.

The sample processing module also includes at least one standardized agitation connector that functions to provide a secure coupling between the sample processing module and an agitator. A variety of agitation connectors are contemplated, and any method of securing the sample processing module to an agitator should be considered to be within the present scope. For example, as is shown in FIG. 1, the standardized agitation connector 18 can be holes in the housing to allow the housing to be bolted or otherwise secured to the agitator. Other examples can include clips, elastomeric materials, magnetic forces, etc. In one specific example, the standardized agitation connector can be a plurality of holes in the housing and a plurality of bolts or screws.

Figure 2:
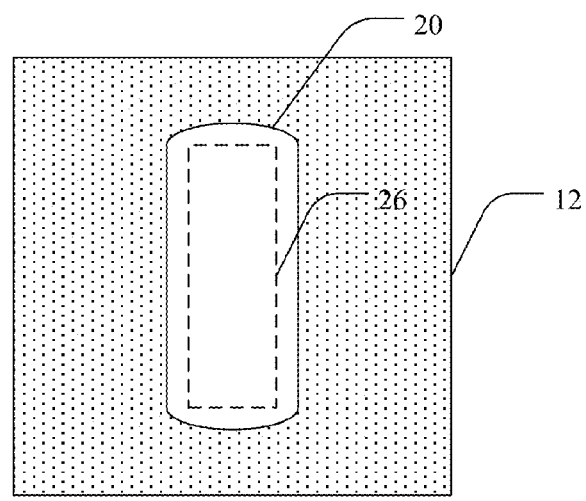
FIG. 2 is a top view of one configuration for a sample processing module having a single open space sufficient to hold a microscope slide in accordance with one embodiment of the present invention.

Various physical configurations of sample processing modules are contemplated in order to accommodate a wide variety of sample processes. Numerous aspects of sample processing modules include internal spaces utilized for processing samples in a volume of fluid. For example, FIG. 2 shows a housing 12 having an internal space 20. The internal space is sized, in this case, to hold a single sample process insert 26 such as a microscope slide. Thus the housing would include the standardized components discussed above (not shown) that would provide fluid, heat, and agitation to the internal space to process the sample contained on the microscope slide. Non-limiting examples of sample processes that can be performed using a microscope slide or similar structure include FISH processing, including prehybridization, hybridization, and post hybridization steps, Hematoxylin and Eosin (H&E) staining, slide processing in immuno-histochemistry, immuno-histopathology, and immuno-cytochemistry, microarrays, sectional in situ hybridization, and the like. Additionally, any sample process using an open bath-type protocol can be processed using such a module. Examples can include post gel or post blot processing, such as with Western, Southern, and Northern blots. As has been described, a sample insert containing sample baskets can also be used in the internal space to process embryos and other small tissue sections, such as would be the case with WISH processing.

Figure 3:
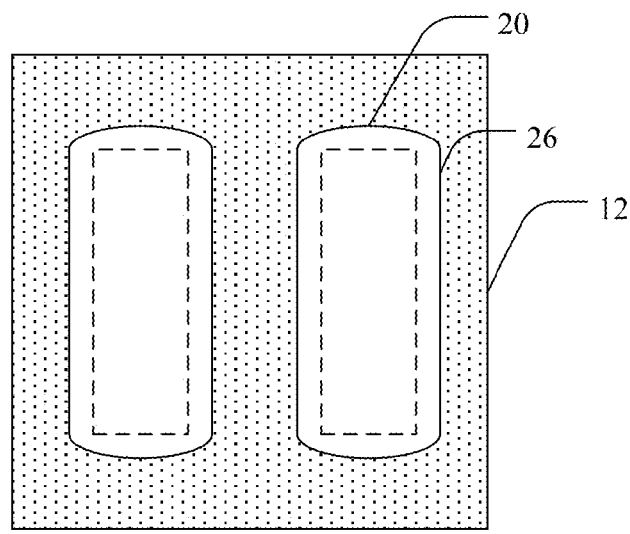
FIG. 3 is a top view of one configuration for a sample processing module having two open spaces sufficient to hold each hold a single microscope slide for tandem or serial processing in accordance with one embodiment of the present invention.
Figure 4:
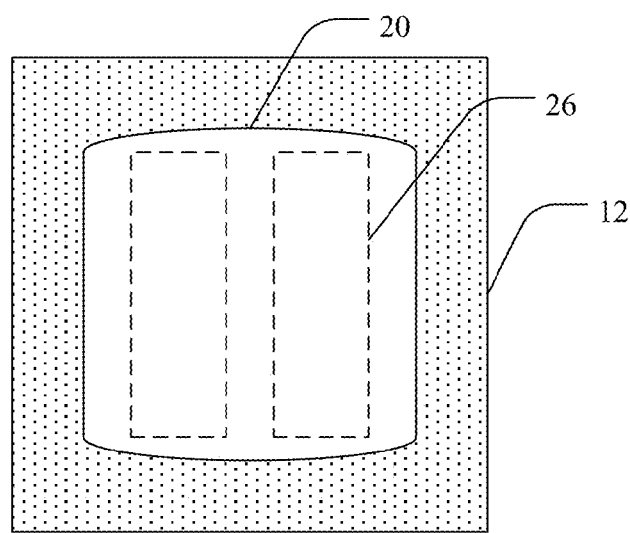
FIG. 4 is a top view of another configuration for a sample processing module having one open space sufficient to hold two microscope slides for simultaneous processing in accordance with one embodiment of the invention.

FIG. 3 shows a sample processing module having a housing 12 and two internal spaces 20 for processing two sample process inserts 26. Thus two processes can occur in the same module having essentially the same heating and agitation inputs. These two samples can be processed with or without similar fluid characteristics, however. FIG. 4 shows a sample processing module having a housing 12 and a single internal space 20 that is sized such that multiple sample process inserts 26 can be processing concurrently in the same internal space. A larger internal space can also be utilized to accommodate larger blot or gel materials. It is also contemplated that a module housing can have multiple internal spaces, where each internal space can process multiple sample process inserts simultaneously. Sample processing modules can also be configured to accommodate electrophoretic gels, well plates, ELISA slide, PCR media, and the like.

It is also contemplated that a sample processing module insert can be introduced into the internal space of a sample processing module, and that the insert can provided an added level of diversity. For example, an open bath type module can have an internal space that is configured to receive and horizontally process one or more microscope slides. This internal space can be used to process slides, blots, or other media that can be processed using an open bath. An insert can be introduced into the internal space that modifies this functionality. As one example, an insert comprising a support holding one or more baskets can be used to perform embryo or other tissue protocols such as WISH processing. In another example, an insert having a plurality of vertically positioned microscope slides can be inserted into the internal space to simultaneously process multiple slides in a vertical orientation.

Figure 5A:
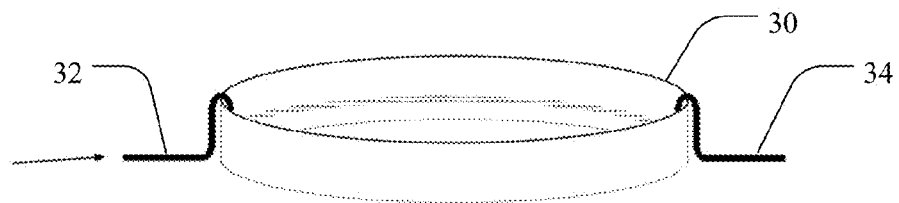
FIGS. 5a-b are perspective views of yet another configuration for sample processing modules having an circular shape dish-type area for receiving samples to be processed in accordance with yet another embodiment of the present invention.
Figure 5B:
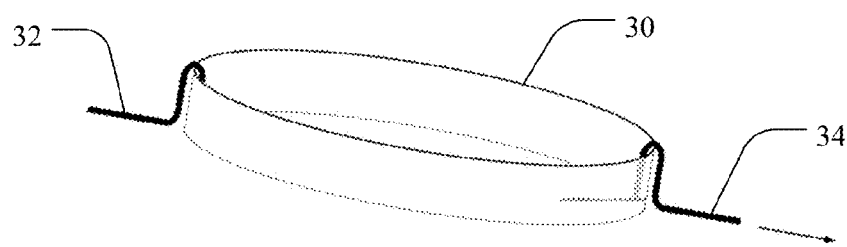

In another aspect, as is shown in FIGS. 5a and 5b, the sample processing module can be a dish 30 such as, for example, a cell culture. The module can include a fluid input clip 32 and a fluid output clip 34. The dish 30 can be filled with fluid from the fluid input clip 32 and subsequently emptied by the fluid output clip 34. FIG. 5a shows the dish 30 in a tilted configuration to facilitate the removal of fluid from the dish 30.

Figure 6:
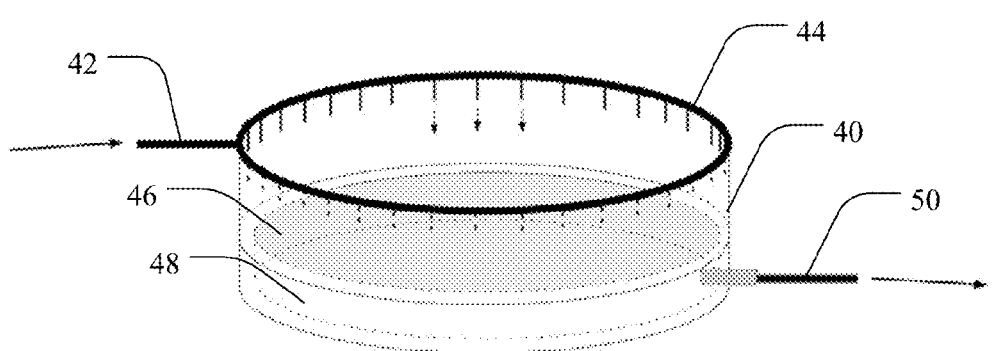
FIG. 6 is a perspective view of a configuration for the sample processing module that includes a filter in accordance with an additional embodiment of the present invention.

In yet another aspect, as is shown in FIG. 6, the sample processing module can be a filtering module 40 for filtering, for example, a sample liquid. The filter module 40 can include a fluid input 42 having a fluid distribution ring 44 around the fluid module to more evenly distribute the fluid. The fluid passes through a filter 46, into a fluid catch reservoir 48, and out of a fluid outlet 50. The sample being processed can be the fluid being filtered or it can be the filter itself, and the fluid is merely a wash step of a laboratory protocol.

As has been described, a sample processing module can be used for a WISH laboratory protocol. A variety of configurations are contemplated, including sample processing modules specific to WISH and WISH inserts to be inserted into an open bath sample process module. One feature of either aspect can include WISH baskets to hold embryos or tissue. A WISH basket can include a screen portion to allow fluid flow to access the WISH sample. The screen can typically be from about 50 to about 150 mesh. The basket can be entirely or partially made of a screen material to allow fluid access. When agitation is applied, the rocking motion allows the fluid within the WISH module to wash the sample. Thus the WISH basket is designed such that fluid can enter from the outside of the basket. In one aspect, the bottom of the basket can be made from a screen material. Thus as fluid enters and rises up and down inside the WISH basket, the sample is maintained in suspension while providing a gentle agitation.

Figure 7:
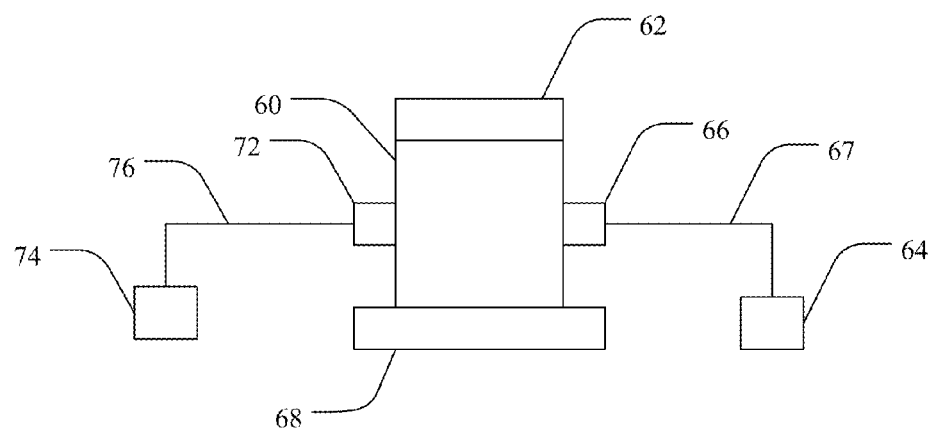
FIG. 7 shows a schematic diagram of a modular sample processing system and method for performing laboratory protocols in accordance with one embodiment of the present invention.

The present invention additionally provides systems for performing laboratory protocols. These systems can incorporate one or more sample processing modules to process one or more laboratory protocols concurrently. In one aspect, as is shown schematically in FIG. 7, a system can include at least one sample processing module 60, and a temperature control system 62 interfaced with the standardized temperature input (not shown) of the sample processing module and configured to regulate temperature of the pre-identified sample process. The system can also include an inlet fluid controller 64 interfaced with the standardized fluid input 66 and configured to deliver fluid via an input fluid line 67 to the sample processing module. The fluid can be withdrawn from a fluid reservoir (not shown) by the outlet fluid controller 74. An agitator 68 is interfaced with the sample processing module 60 and configured to provide agitation, and a control system (not shown) is interfaced with the temperature control system 62, the inlet fluid controller 64, and the agitator 68, and is configured to control temperature, fluidics, and agitation of the sample processing module. It should also be noted that in some aspects multiple sample processing modules can be concurrently utilized in the system. Furthermore, in some aspects, multiple sample processing modules that are concurrently used can have a different pre-identified sample process.

The system can additionally include a standardized fluid output 72 associated with the sample processing module 60 and interfaced with an output fluid controller 74. The standardized fluid output 72 and the output fluid controller are configured to remove fluid from the sample processing module via an output fluid line 76. In one aspect, output fluid controller can deliver the output fluid to a waste container (not shown).

The system can include a variety of input fluidics. In general, the input fluidics should include all components that are necessary to move fluid from a fluid reservoir into the sample processing module. Thus the standardized fluid input associated with the sample processing module can include couplings, fittings, channels, pipes, open receptacles, and any other technique or device to associate fluidics with the module. The input fluid controller removes fluid from a fluid reservoir and transfers that fluid into the sample processing module. In one aspect, such a transfer of fluid can be accomplished via fluidics tubes or channels that are fluidically coupled from the fluid reservoir to the standardized fluid input. In one aspect, the input fluid controller can be a pumping mechanism. A variety of pumping mechanisms can be utilized to perform the various pumping functions of the present invention. Non-limiting examples of such pumping mechanisms can include peristaltic pumps, syringe pumps, screw pumps, piston pumps, and the like. In another aspect, the transfer of fluid can be discontinuous, as would be the case for systems where the standardized fluid input was an open receptacle and the fluid input controller was a pipette or other discontinuous fluid transfer device. Such a discontinuous fluid transfer system can be facilitated by utilizing a robotic arm attachment in conjunction with the fluidics system. A variety of fluids can be delivered using the various fluid input mechanisms and supporting hardware described herein, as well as others known to those of ordinary skill in the art. Examples of such fluids include without limitation, fluids containing samples for processing, (i.e. sample presented in a fluid form) buffer fluids, reagent fluids, wash fluids, etc.

Figure 8:
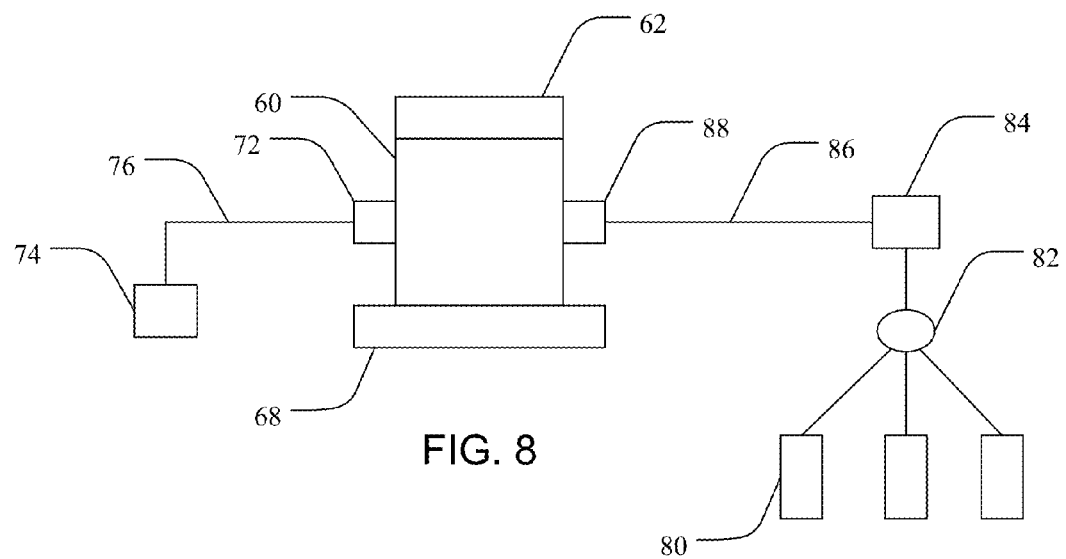
FIG. 8 shows a schematic diagram of a modular sample processing system and method for performing laboratory protocols in accordance with one embodiment of the present invention.

In one aspect, as is shown in FIG. 8, the input fluidics system can deliver fluids from multiple fluid reservoirs 80. An input fluid distribution valve 82, such as a rotary value, can engage a fluid line from a specific fluid reservoir 80 in order to deliver a particular fluid to the sample processing module 60. The input fluid controller 84 can draw the selected fluid through the input fluid distribution valve 82, through the input fluid line 86 and to the sample processing module 60 via the standardized fluid input 88. A different fluid can be delivered by merely switching the input fluid distribution valve 82 to a different position, thus selecting a different fluid reservoir. Depending on the configuration of the sample processing module, the input fluid line 86 can be a single fluid line or multiple fluid lines. Similarly, the standardized fluid input 88 can be a single input or multiple inputs. Furthermore, additional input fluid distribution valves can be utilized at any point along the fluid line to further distribute the fluid.

Utilizing input and output fluid distribution valves allows fluid to be added and withdrawn from the sample processing module with specific timing and in a specific order. In one aspect, for example, fluid is drawn and delivered to a valve switches between various fluid lines delivering fluid to the sample processing modules. Thus the delivery of fluid to the sample modules can be accurately timed. The ability to deliver reagent with one pump and withdraw reagent with another pump can be very beneficial in timing reactions occurring in the sample modules. Thus reagent can be sequentially delivered to a plurality of sample modules and subsequently removed following a given incubation time to facilitate a uniform reaction time across all sample modules. It is additionally contemplated that in some cases reaction times may vary between sample modules, yet still be precisely controlled as to incubation time for a given sample module.

Figure 9:
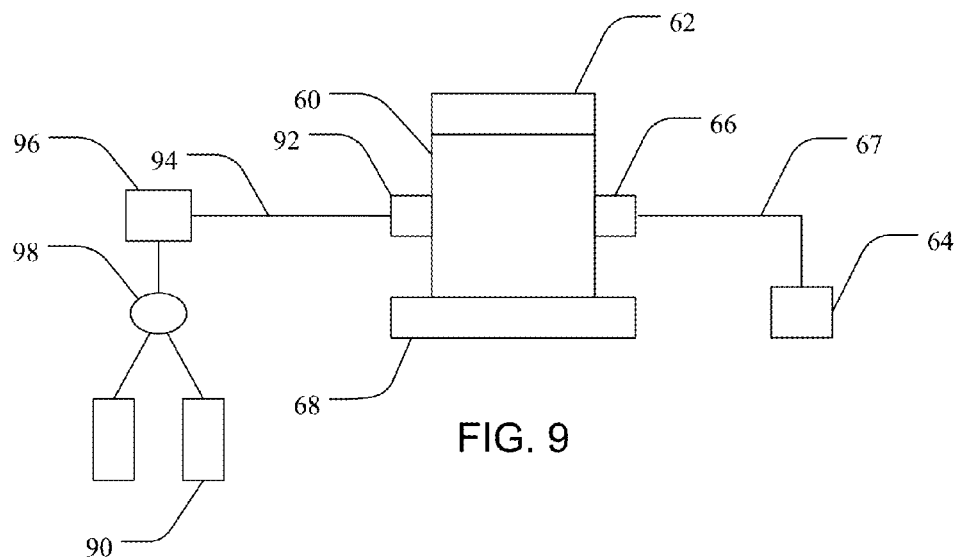
FIG. 9 shows a schematic diagram of a modular sample processing system and method for performing laboratory protocols including a fluidics system in accordance with one embodiment of the present invention.

In one aspect, as is shown in FIG. 9, the output fluidics system can withdraw fluids from the sample processing module 60, and deliver that fluid to multiple output fluid containers 90. Output fluid can be withdrawn from a standardized fluid output 92, and delivered through a fluid output line 94 by the output fluid controller 96. An output fluid distribution valve 82, such as a rotary value, can be used to select an output fluid container 90 into which the fluid will be transferred. Thus fluids from different sample processes or sample process steps can be partitioned to different output fluid containers. Depending on the configuration of the sample processing module, the output fluid line 92 can be a single fluid line or multiple fluid lines. Similarly, the standardized fluid output 92 can be a single output or multiple outputs. Furthermore, additional fluid distribution valves can be utilized at any point along the fluid line to further distribute the fluid.

Figure 10:
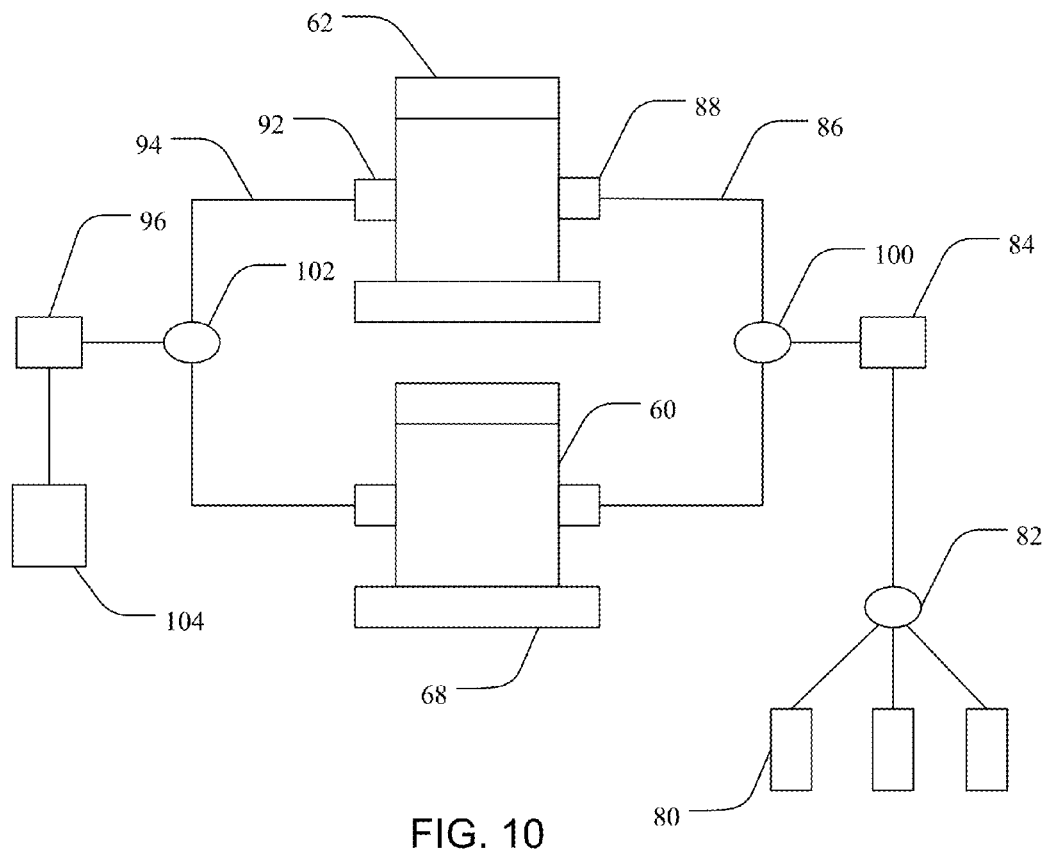
FIG. 10 shows a schematic diagram of a yet another configuration for a modular sample processing system and method for performing laboratory protocols including a fluidics system in accordance with one embodiment of the present invention.

FIG. 10 shows an aspect of the present invention having multiple sample processing modules 60 and multiple fluid reservoirs. In this aspect, an input module fluid distribution valve 100 is utilized to selectively route fluid to each sample processing module. Additionally, an output module fluid distribution valve 102 is utilized to selectively remove fluid from each sample processing module for delivery to a waste container or other output fluid reservoir 104. It should be noted that further distribution of the output fluid is contemplated, similar to what is shown in FIG. 9.

Figure 11:
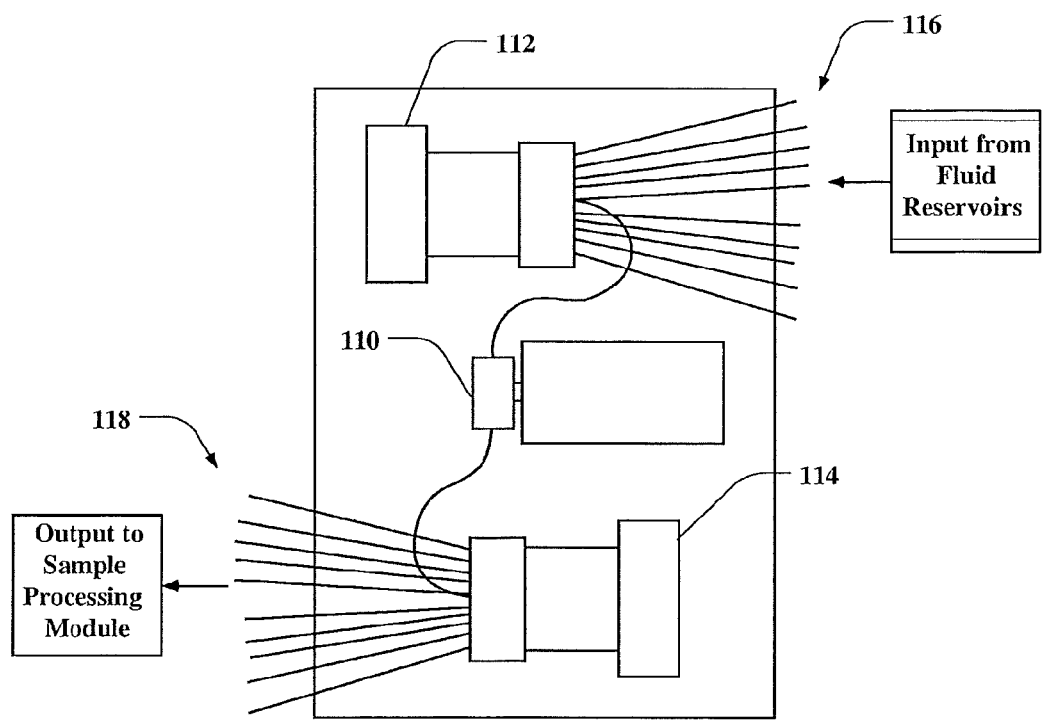
FIG. 11 shows a schematic diagram of input fluidics in accordance with one embodiment of the present invention.

In one aspect of the present invention, as is shown in FIG. 11, an input fluid controller can include a pumping mechanism 110 fluidically coupled to a first fluid distribution valve 112 and a second fluid distribution valve 114. In this configuration, the first fluid distribution valve 112 is positioned to engage a fluid input line from a plurality of fluid input lines 116. The plurality of fluid input lines are coupled to a plurality of fluid reservoirs (not shown) containing the various buffers, washes, reagents, etc. that are to be used for a particular sample process. The second fluid distribution valve 114 is positioned to engage a fluid output line from a plurality of fluid output lines 118 that are coupled to a plurality of destination points associated with the sample processing module. A plurality of output lines can couple to a single sample processing module or multiple sample processing modules. The pumping mechanism 110 can then be engaged to draw a selected fluid through the fluid input line and out the output fluid line to the sample processing module. By switching the second fluid distribution valve 114, the selected fluid can be delivered through various of the plurality of output lines 118 to various sample processing locations. Switching the first fluid distribution valve 112 to another fluid input line allows subsequent fluids to be drawn from different fluid reservoirs and delivered via the second fluid distribution 114 to the various sample processing locations.

Figure 12:
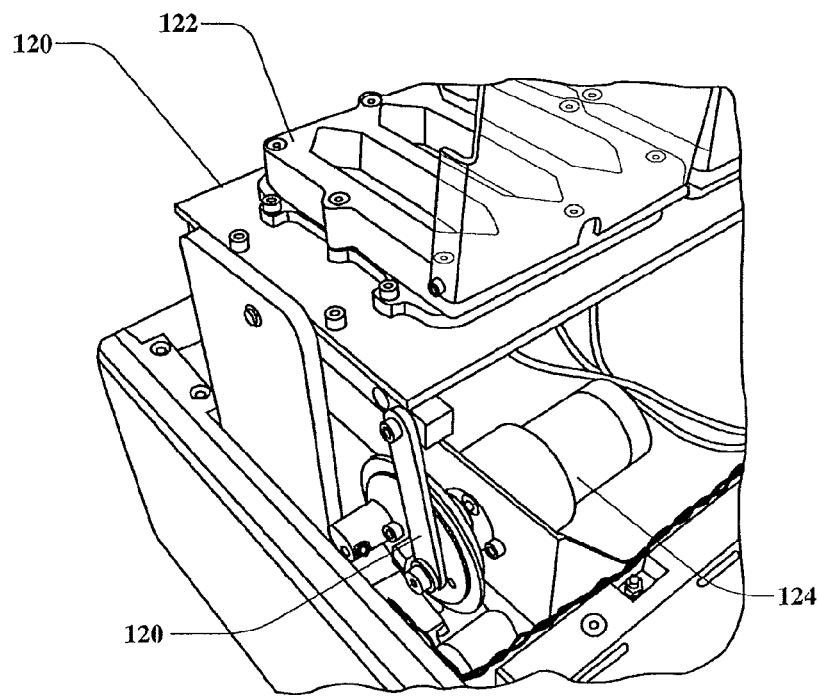
FIG. 12 shows a perspective view of an agitation system in accordance with one embodiment of the present invention.

An agitator can be included in the present systems in order to provide agitation to the sample processing module. The agitator can be any means of agitation known, and can be provided in fixed and variable speeds. In one aspect, as is shown in FIG. 12, the agitator can include a mounting plate 120 for mounting the sample processing module or modules 122. A motor 124 or other motion generating device can be coupled to the mounting plate 120 with an adjustable coupling device 126. The adjustable coupling device 126 can be adjusted to vary the travel of the mounting plate 120 and thus provide a variety of motions to the sample processing module. Such motions can include vibration, back and forth motion, circular motion, rocking motion, and the like.

The agitator can function in conjunction with the fluidics system in order to facilitate removal of fluid from the sample processing module. For example, a module can be filed with fluid and rocked back and forth to provide agitation to the sample process. To remove a fluid, the agitator can move to a tilted position such that fluid can accumulate at the standardized fluid output in order to facilitate fluid removal. As an example, a sample processing module can be agitated at a slight rocking tilt, such as 10°, during a wash step. Once the wash is finished, the agitator can tilt the sample processing module to a greater angle, such as 30°, in order to drain the fluid from the module. It should be noted that the angles described in association with agitation are intended to be merely exemplary. As such, various ranges of angles could be used in a similar manner to what is described.

The agitator can be configured to provide a constant back and forth travel, or it can be configured to provide a variable travel. For example, the mounting plate can be rocked with a steeper slope on the forward motion and a lesser slope on the backward motion. Additionally, the mounting plate can be maintained in an angled position to facilitate the removal of fluids from the sample modules. The motor can be a variable speed motor, thus allowing changes in agitation frequency as well as amplitude. Additionally, positional sensors on the motor can allow the mounting plate to be held horizontally to allow even fluid coverage of the samples, or held in an angled position to allow draining.

In one aspect, a single mounting plate can be configured such that multiple sample processing modules can be agitated concurrently. In another aspect, a separate mounting plate can be utilized for each module to allow non-concurrent agitation. Thus laboratory protocols can be run simultaneously that have different agitation steps, or that are spaced in time such that concurrent agitation is not desirable.

The system can further include a control system to facilitate the laboratory protocol steps in the various parts of the system. The control system can regulate temperature, agitation, fluid control, including fluid input and output, and can manage multiple sample processing modules simultaneously. The control system can include a user interface to allow the selection or input of the steps of the laboratory protocol, as well as specific parameters that may be useful for a particular protocol. The control system can also allow user control over some or all of the steps of a laboratory protocol, to all the protocol to be paused, halted, portions repeated, and the like. Such systems are well known, and it would be considered within the skill of one of ordinary skill in the art to implement such a control system in conjunction with the present system. Additionally, it should be noted that the control system can communicate with the various components via wired or wireless communication.

In one aspect of the present invention, the control system can be a software controller. Such a controller can be used to cause the system to perform a laboratory protocol with varying degrees of interaction by a user. For example, in one aspect, the user can merely load samples into sample modules, associate reagents with reagent input fluidics, and start the software controller. The software controller can thus deliver and withdraw reagents, manage timing of reactions, apply proper agitation, heating, cooling, and the like. Numerous software control systems are contemplated, and any such controller or system should be included within the present scope. In one aspect, a laboratory protocol can be set up using a spread sheet program, and such a spread sheet can be used to execute the protocol. In one aspect, for example, the spreadsheet can be saved as a comma delimited file and executed using a program such as Python.

The following is a general example of how a modular system can function. It should be noted that the steps outlined herein can vary depending on the protocol being performed, and as such, these steps should not be seen as limiting. A user initially obtains reagents that are needed for a particular protocol. The user can place the reagents in containers, or obtain reagent containers having reagents already therein. The user then associates tubes from a reagent valve in the inlet fluidics module to the appropriate reagent containers. The user can then enter timing, temperature, and agitation motion for each protocol step into a control interface associated with the system. An appropriate sample can be introduced into the sample processing module and the protocol steps can be initiated.

A pump draws a reagent from the assigned reagent container into the tubing that runs from the reagent container through the reagent valve, through the pump, and into the sample valve in the input fluidics system. Excess reagent can be exited through a waste tube in the sample valve. It can be beneficial to clear previous reagent from a fluid line when reagents are changed. As such, when a new reagent is used, a small amount of the new reagent can be drawn through the first valve, through the pump and the second valve into a waste container. This will clear the fluid lines up to the second valve of the previous reagent. Reagent is drawn and dispensed through the sample valve to sequentially fill each sample chamber of the sample module. If heat or cooling is required, a heating module can be activated to raise or lower the temperature of the sample chamber(s). The sample incubates in the reagent for the designated length of time at the required temperature. Agitation can be applied.

The pump can then draw a second reagent from the assigned reagent container to fill the tubing from the assigned reagent container through peristaltic pump and to the sample valve. Excess second reagent exits through waste tube from sample valve. The system continues to draw the second reagent through the sample valve to sequentially fill each sample chamber, thereby displacing the first reagent in each chamber through waste port and tube. A sufficient amount of second reagent is drawn to completely replace the preceding reagent in the sample chambers. The heating module can heat the sample chambers again if required. The sample incubates with the second reagent for the designated length of time at the required temperature. Again, agitation can be utilized. The system continues as described above until the protocol is completed. The user can then remove the sample from the sample processing module when the automated portion of the protocol is complete.

Figure 13:
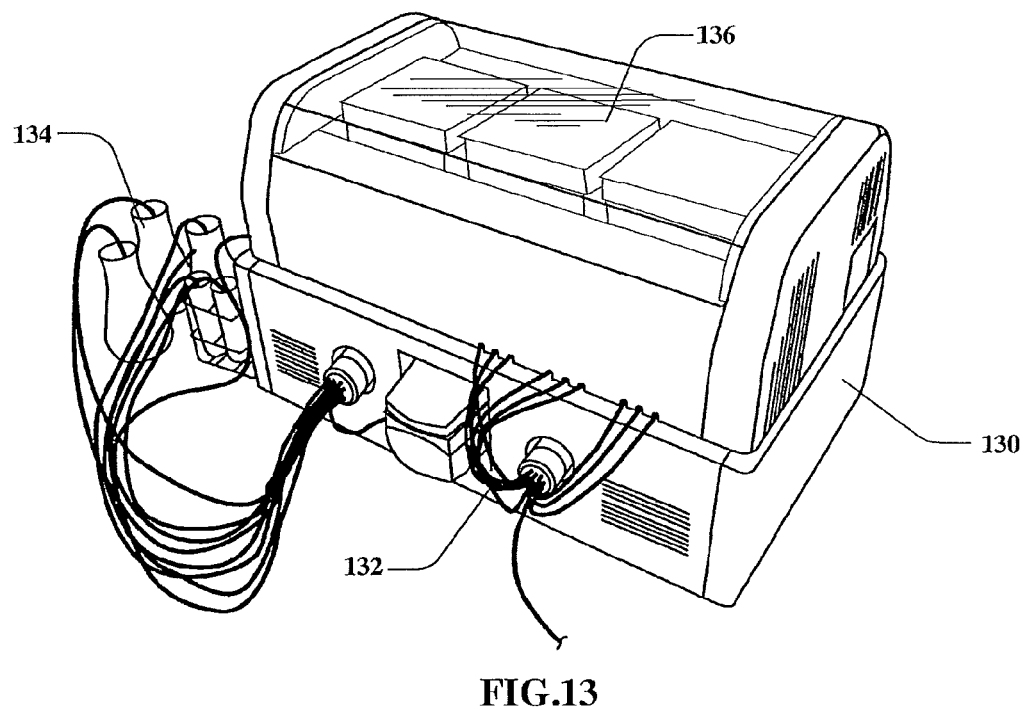
FIG. 13 shows a perspective view of a modular sample processing device and system having three interchangeable sample processing modules in accordance with one embodiment of the present invention.
Figure 14:
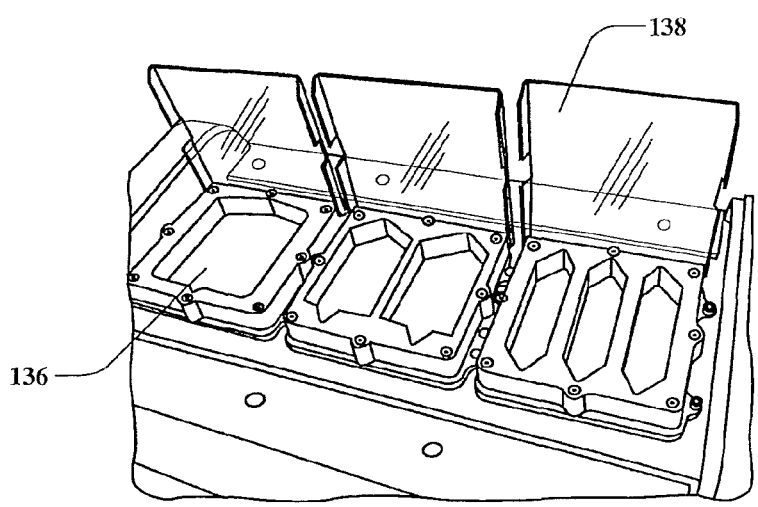
FIG. 14 shows a perspective view of a modular sample processing device and system having three interchangeable sample processing modules in accordance with one embodiment of the present invention.

The following is a general example of a modular sample processing system. It should be noted that detail and structure outlined herein can vary, and as such, these details and structures should not be seen as limiting. Accordingly, FIG. 13 shows a modular system for performing various sample processes. FIG. 13 shows various details of the system, including a housing 130, input fluidics 132, reagent or fluid reservoirs 134, and a lid covering a plurality of sample processing modules 136. Upon removing the lid, various sample processing modules 136 can be seen in FIG. 14. The sample processing modules can include a sample processing module lid 138 to contain liquids during agitation and to reduce evaporation. The lid 138 can be clear as shown, or opaque to protect any light sensitive samples from ambient light. Also, a gasket can be provided between the lid and the sample processing module to further prevent spilling and evaporation.

Figure 15:
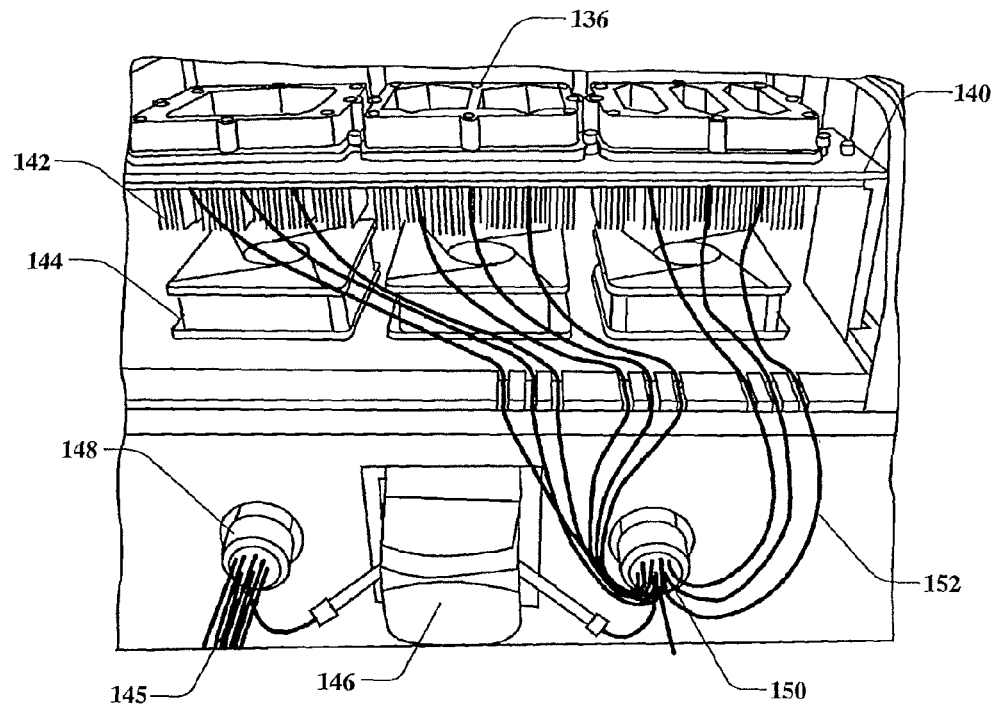
FIG. 15 shows a perspective view of a thermal regulation system and input fluidics of a modular sample processing device and system in accordance with one embodiment of the present invention.

FIG. 15 shows additional detail of the system. Sample processing modules 136 are secured to a mounting plate. A thermal regulation system including thermal fins 142 and Peltier elements (not shown) are associated with the sample processing modules 136. Fans 144 can further facilitate thermal regulation as has been described herein. A pump 146 is coupled to a first rotary valve 148, which is in turn coupled to a plurality of fluid input lines 145 that coupled to a plurality of fluid reservoirs (not shown). The pump 146 is capable of pumping fluid from the first rotary valve 148 to a second rotary valve 150 and through a series of sample fluid lines 152 to the sample processing modules 136. The sample fluid lines are thus coupled to the sample processing modules. Each sample processing module can have one or more coupled sample fluid lines, depending on the configuration of the modules and the number of internal spaces in each module.

Figure 16:
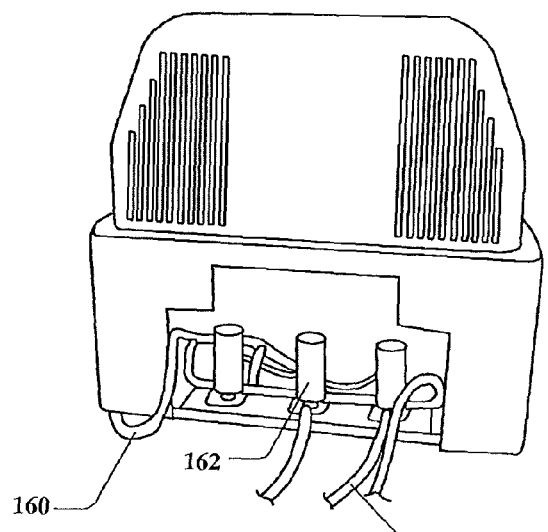
FIG. 16 shows a perspective view of output fluidics of a modular sample processing device and system in accordance with one embodiment of the present invention.

FIG. 16 shows a portion of the waste or output fluid system. A pump (not shown) similar to that shown in FIG. 15, can couple with a rotary valve (not shown) to selectively remove fluids from the sample processing modules. This output fluid can be transmitted through an output fluid line 160 to one or more waste distribution valves 162. The waste distribution valves 162 can be used to distribute output fluid to one or more waste reservoirs (not shown) via waste fluidic lines 164. Waste fluids can thus be sorted and distributed by the rotary valve and the waste distribution valves 162 into appropriate waste reservoirs for disposal or further use. For example, organics can be sorted to one reservoir, while non-organic waste can be sorted to another. In those aspects having a single waste reservoir, the output fluid can be sent directly to the single waste reservoir from the pump without the need for waste distribution valves 162.

Figure 17:
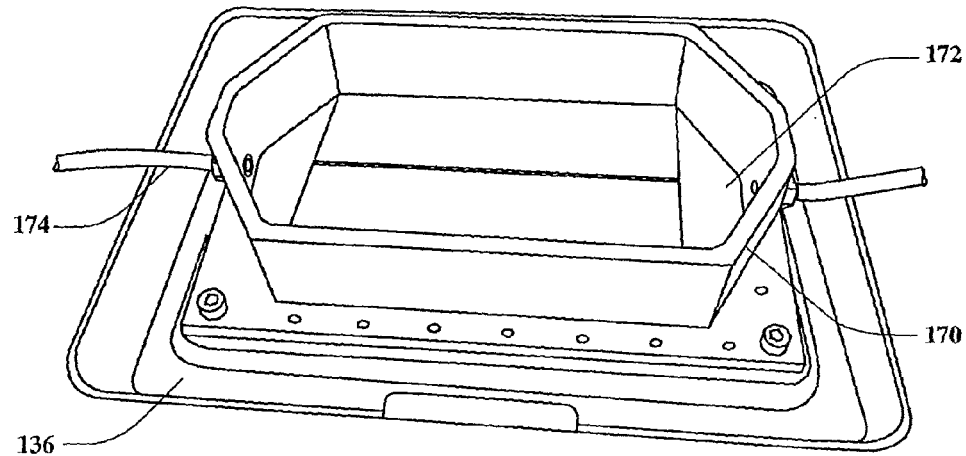
FIG. 17 shows a perspective view of a sample processing module of a modular sample processing device and system in accordance with one embodiment of the present invention.

As has been described, the present system can include a variety of sample processing module inserts and devices that can facilitate sample processing. FIG. 17 shows, for example, a sample processing module 170 having an internal space 172 containing two microscope slides. FIG. 17 shows the output fluidic line 174 for removing waste from the module. Additionally, an overflow channel 176 is shown around the sample processing module 170 to catch spilled fluid. An output (not shown) from the overflow channel can empty passively or actively to a waste container.

Figure 18:
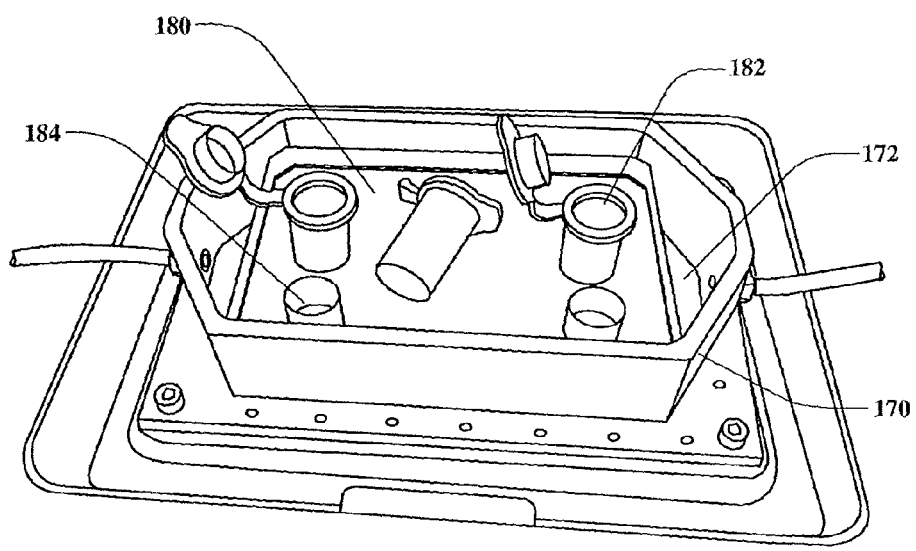
FIG. 18 shows a perspective view of a sample processing module of a modular sample processing device and system in accordance with one embodiment of the present invention.

FIG. 18 shows the sample processing module 170 of FIG. 17 having a WISH basket insert 180 located in the internal space 172. The WISH basket insert 180 is configured to hold one or more WISH baskets 182 in one or more holes 184 present in the insert. The holes allow the fluid in the internal space 172 to reach the WISH basket 182 as has been described herein.

Figure 20:
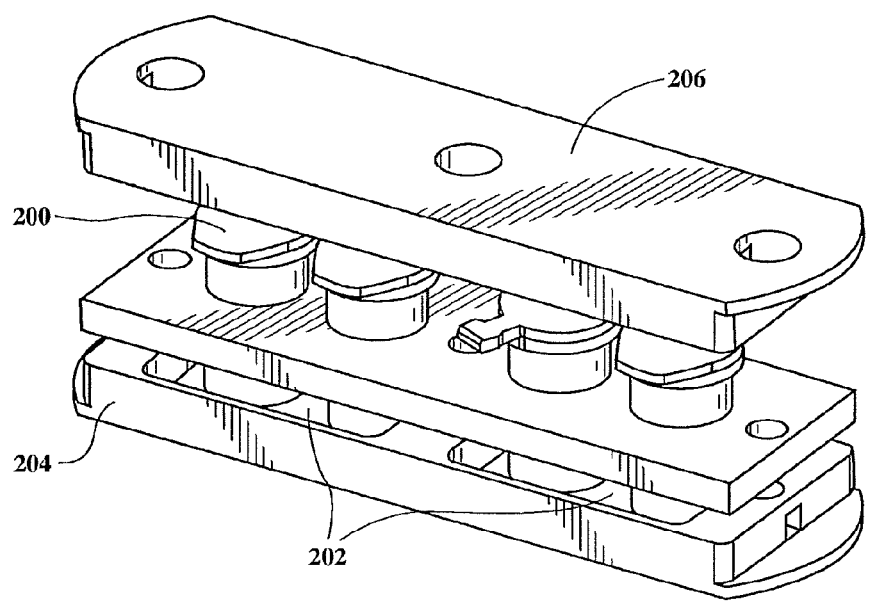
FIG. 20 shows a perspective view of a basket clamp device in accordance with one embodiment of the present invention.

For some steps such as the hybridization, however, the fluid used in WISH can be very valuable and as such it may be desirable to use as little as possible (e.g. 100 µl). Accordingly, for such fluid-saving steps, the liquid may not be pumped through the system but rather would be added manually to the WISH basket. Such manual addition can be facilitated by capping the bottom of the WISH basket. In one aspect, the bottom of the WISH basket can be sealed or clamped with a material such as Parafilm®. FIG. 20 shows such a clamping device. Thus the sample and the hybridization fluid can be added to the basket 200. A Parafilm® 202 or other similar material can be placed in a base portion 204 of the clamp, and a cap portion 206 can be used to clamp the device together and provide sufficient pressure to seal the baskets with the Parafilm®.

Figure 19:
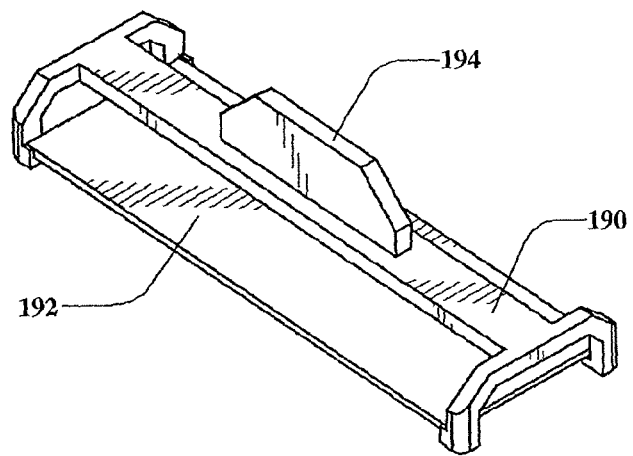
FIG. 19 shows a perspective view of a microscope slide carrier in accordance with one embodiment of the present invention.

In another aspect, as is shown in FIG. 19, a slide carrier 190 can be used to couple to a microscope slide 192 to facilitate transport and use. A handle 194 can be coupled to the slide carrier to further facilitate handling. The slide carrier 190 can be configured to allow a space to be formed between the sample processing module and the microscope slide 192 to allow fluid to more readily flow across the bottom surface of the slide. In this manner the slide can be processed with the sample material located on the slide being oriented downward. This allows the sample material to be more fully immersed in the fluid and can reduce splashing turbulence that can occur on the surface of the fluid from contacting the sample material.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A sample processing module, comprising:
   a housing including an internal space configured to contain a sample on a sample process insert to accommodate a pre-identified sample process;
   a standardized temperature input capable of interfacing with a temperature controller and in heat transfer communication with the housing;
   a standardized fluid input capable of interfacing with an input fluid controller and configured to fluidically couple with a fluid line to deliver fluid to the internal space in the housing to contact the sample in the internal space; and a standardized agitation connector coupled with an agitator and coupled to the housing to provide agitation of the housing;

wherein the standardized components provide interchangeability of the module with a module having a housing configured to accommodate a different pre-identified sample process in a sample processing system.

2. The sample processing module of claim 1, further comprising the sample process insert configured to insert into the internal space.

3. The sample processing module of claim 2, wherein the sample process insert includes a member selected from the group consisting of a microscope slide, a microarray, a sample basket, a blot, a filter, an ELISA insert, and combinations thereof.

4. The sample processing module of claim 1, wherein the pre-identified sample process includes a member selected from the group consisting of in situ hybridization, Western blots, Northern blots, Southern blots, slide processing, immunohisto chemistry reactions, histopathology reactions, antibody assays, gel electrophoresis, restriction analysis, ligation, labeling, filter-based assays, and combinations thereof.

5. The sample processing module of claim 1, wherein the pre-identified sample process includes a member selected from the group consisting of fluorescent in situ hybridization, whole mount in situ hybridization, and combinations thereof.

6. The sample processing module of claim 1, wherein the standardized fluid input is configured to fluidically couple with a fluid line, and the input fluid controller is a pump system.

7. The sample processing module of claim 1, wherein the standardized fluid input is an open receptacle and the input fluid controller is a pipette.

8. The sample processing module of claim 1, further comprising a standardized fluid output capable of interfacing with an output fluid controller.

9. The sample processing module of claim 8, wherein the standardized fluid output is configured to fluidically couple with a fluid line, and the output fluid controller is a pump system.

10. The sample processing module of claim 8, wherein the standardized fluid output is an open receptacle and the output fluid controller is a pipette.

11. The sample processing module of claim 1, wherein the temperature input is a thermally conductive surface.

12. The sample processing module of claim 11, further comprising a Peltier system thermally coupled to the thermally conductive surface.

13. A system for performing a laboratory protocol, comprising:

at least one sample processing module as recited in claim 1;

a temperature control system interfaced with the standardized temperature input and configured to regulate temperature of the pre-identified sample process;

an inlet fluid controller interfaced with the standardized fluid input and configured to deliver fluid to the pre-identified sample process;

an agitator interfaced with the sample processing module and configured to provide agitation to the pre-identified sample process; and a control system interfaced with the temperature control system, the inlet fluid controller, and the agitator, and configured to control temperature, fluidics, and agitation of the pre-identified sample process.

14. The system of claim 13, wherein the at least one sample processing module is a plurality of sample processing modules.

15. The system of claim 14, wherein at least two of the plurality of sample processing modules have a different pre-identified sample process.

16. The system of claim 13, further comprising:

a standardized fluid output associated with the sample processing module; and an output fluid controller interfaced with the standardized fluid output and configured to remove fluid from the pre-identified sample process.

17. The system of claim 16, wherein the output fluid controller is coupled to the standardized fluid output a fluid line, and the output fluid controller is a pump system.

18. The system claim 16, wherein the standardized fluid output is an open receptacle and the output fluid controller is a pipette.

19. The system of claim 13, wherein the input fluid controller is coupled to the standardized fluid input with a fluid line, and the input fluid controller is a pump system.

20. The system of claim 13, wherein the standardized fluid input is an open receptacle and the input fluid controller is a pipette.

21. The system of claim 13, further comprising a robotic arm attachment operable to interface with the pre-identified sample process.

22. A method of processing samples according to different pre-identified sample processes using a single sample processing system comprising:

configuring a modular sample processing system as recited in claim 13 to accommodate at least one pre-identified sample process; and processing a sample using the sample processing system to execute the pre-identified sample process.

23. The method of claim 22, wherein at least two different pre-identified sample processes are executed in different sample modules using the sample processing system.

24. The method of claim 22, further comprising removing one or more sample modules from the sample processing system upon completion of sample processing and inserting one or more new sample modules configured to accommodate sample processes different from the removed modules; and processing new samples according to new pre-identified sample process with the sample processing system.

* * * * *